United States Patent [19]

Hill

[11] 4,258,704
[45] Mar. 31, 1981

[54] BODY ORIFICE ACCESSORY

[75] Inventor: Roger C. Hill, Skipton, England

[73] Assignee: Johnson & Johnson, New Brunswick, N.J.

[21] Appl. No.: 938,149

[22] Filed: Aug. 30, 1978

[51] Int. Cl.³ .................................................. A61B 19/00
[52] U.S. Cl. ........................................ 128/1 R; 128/270; 128/283; 128/285
[58] Field of Search ................ 128/1 R, 283, 285, 270

[56] References Cited

U.S. PATENT DOCUMENTS

| | | | |
|---|---|---|---|
| 1,669,295 | 5/1928 | Hallenberg | 128/270 X |
| 2,931,353 | 4/1960 | Kitzul | 128/1 R |
| 3,958,556 | 5/1976 | Schenk | 128/1 R |
| 4,117,847 | 10/1978 | Clayton | 128/283 X |
| 4,121,589 | 10/1978 | McDonnell | 128/283 |

*Primary Examiner*—Dalton L. Truluck
*Attorney, Agent, or Firm*—Irving Newman

[57] ABSTRACT

A stoma closure, to be secured to the stoma periphery by means of a flexible adhesive sheet, comprises an absorbent flexible closure plug such as a disposable tampon for insertion within the lumen of the stoma passage, and an abutment retained on the distal end of the plug by means embracing the distal end, for placement under the adhesive sheet. The abutment may for instance be a ferrule fixed or detachably locked on the end of the plug, or a disc wider than the plug and enveloped in the same covering as the plug.

10 Claims, 2 Drawing Figures

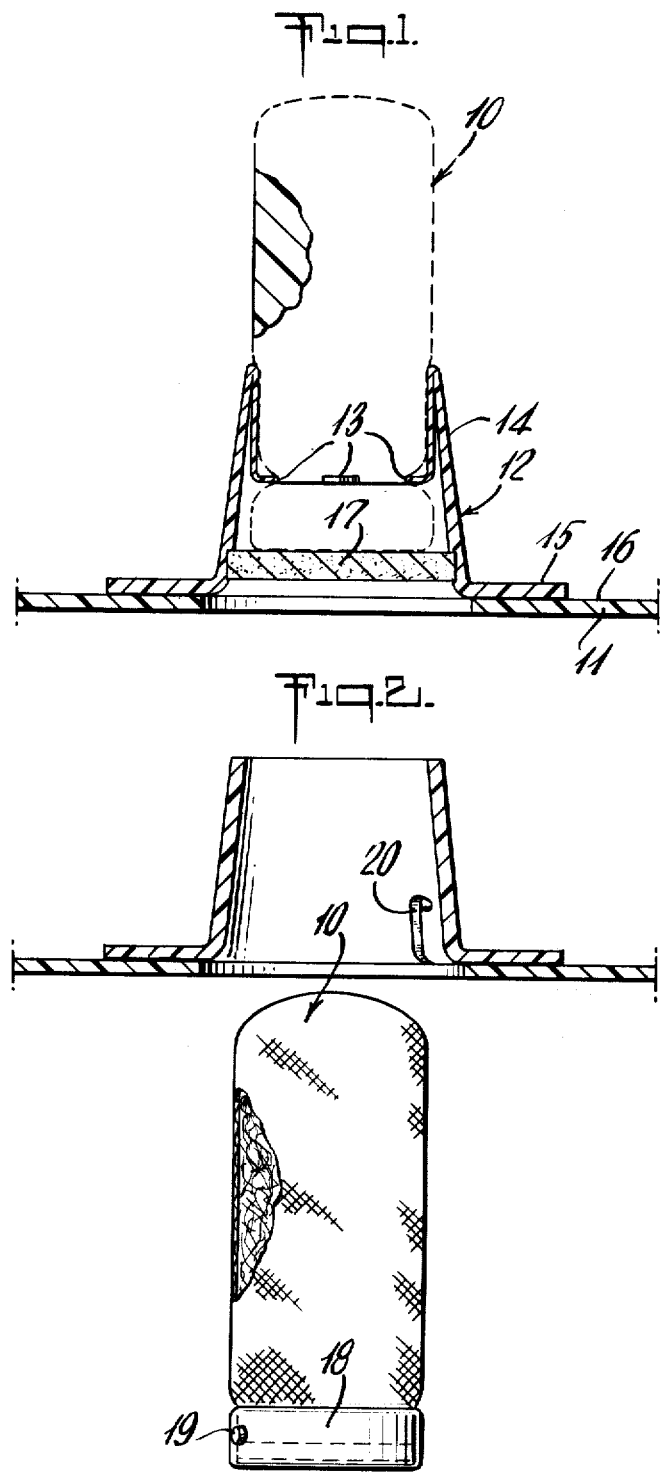

BODY ORIFICE ACCESSORY

BACKGROUND OF THE INVENTION

1. Field of the Invention

The invention relates to an accessory for a body orifice, by which we mean an external opening in an internal passage of a living body. The accessory takes the form of an abutment for use in providing a closure for such an opening. The invention is applicable by way of example in a stoma closure such as may be used in sealing an artificial anus, and will be further described for convenience in that context although it is evidently applicable more generally to orifices whether artificial or not.

The invention accordingly relates more particularly to a device for sealing an artificial anus by means of a flexible closure plug introduced into the lumen of the intestine of the artificial anus, the device comprising an abutment portion for laying on the outside of the body, generally the abdominal wall of the user. 2. Description of the Prior Art Devices of this kind have previously been proposed, in which the sealing apparatus has a partially inflexible external portion and a flexible cushion-like, internal portion (U.S. Pat. No. 2,564,399 and U.S. Pat. No. 3,447,533). The inflexible portion of the closure plug is intended to extend through the muscular body wall of the user, an abutment portion resting against the outside of the user's body, whilst the flexible portion of the closure plug is intended to be expanded radially behind the body wall in the lumen of the intestine for the purpose of anchoring the device in the artificial anus.

For the purpose of expanding the flexible closure plug section radially, it has been proposed to contract the closure plug axially by means of a chain, string or springs (U.S. Pat. No. 3,447,533). It has also been proposed to make the flexible portion of the closure plug in the manner of an inflatable flexible bladder of rubber or the like, for inflation from the outside by means of a rubber ball (U.S. Pat. No. 2,564,399). In these devices a relatively complicated technical construction is necessary, for achieving the radial expansion of the inserted closure plug. Consequently the device is technically complicated, particularly prone to contamination and difficulty is experienced both in preventing its involuntary release and, in a mechanical sense, in its use by the elderly, who are the principal users of an artificial anus in cases of cancer of the large intestine. Moreover adequate sealing of the artificial anus cannot be accomplished with these previously proposed devices, particularly against intestinal gases and liquids which temporarily distort the flexible, radially expandable closure plug portion and are pushed out past the partially inflexible closure plug portion. The appliances constructed in accordance with the two U.S. Patent Specifications are indisposable and consequently the cleansing required is nauseating.

In practice therefore tightly fitting closures or plastics bags attachable by adhesion continue to be used. These two arrangements however have considerable disadvantages. The known closures have to be pressed on by means of a girdle under fairly substantial pressure in order to seal the artificial anus. Apart from the fact that the wearing of such closures is consequently unpleasant, the use of such closures tends to distort the intestinal tissues and to cause haemorrhages and inflammation. During movements of the body, the closure may moreover become displaced from the artificial anus, so that the latter is frequently exposed. The adhesively attachable plastics bags, on the other hand, are intended and suitable only for collecting, but not for holding back excreta and intestinal gases. Since a person equipped with an artificial anus lacks the facility to hold back excreta and intestinal gases voluntarily and the discharge of excrete and intestinal gases into the plastics bag causes considerable acoustically apprehensible noise and a characteristic smell during bowel movement the user is considerably handicapped socially even when such plastics bags are used properly. The adhesively attached bags moreover have the disadvantage that the weight of the more or less filled plastics bag causes discomfort and may result in the bag becoming involuntarily detached from the user's skin, particularly in summer when the skin perspires. Here also the wearing of a girdle is recommended.

In relation to the foregoing, the invention has the primary object of substantially improving devices for sealing an artificial anus or similar opening by means of a closure plug and abutment portion, in such a way that optimum conditions of cleanliness and simple operation together with comfortable application and reliable sealing are ensured.

It is another object of the invention to provide an abutment portion for such a device, offering distinctive advantages in use, such as facility for changing the closure plug without having to detach the abutment from the body of the wearer.

In British Pat. No. 31230/74 there is described and claimed a device for sealing an artificial anus, said device comprising an elongate, flexible, disposable closure plug made of absorbent material and which is adapted to be introduced into the lumen of the artificial anus, an abutment portion which is adapted to be placed on the outside of the body adjacent the artificial anus, generally on the abdominal wall of the user, said abutment portion being in the form of a disc-shaped flexible support portion and having on the side that is to face the body an annular region of adhesive material compatible with the human skin and adapted to hold the device in place on the user's body while sealing against escape of fluid from the anus, and a connection member for retaining said closure plug with said flexible support portion, said connection member being secured to, and projecting from, said side of said support portion. The connection member described in U.S. Pat. No. 1,485,825 is a helical pin having a head large enough to prevent it being dragged through the abutment portion. As the device is constructed, the closure plug is pushed or twisted onto the pin and thereby locked in place.

SUMMARY OF THE INVENTION

According to the present invention we provide an abutment, for an external opening in an internal passage of a living body, comprising a flexible adhesive sheet adapted to retain an absorbent flexible closure plug within the lumen of the passage by means embracing the distal end of the plug. The invention further provides a device for occluding such an opening, which may or may not be artificial such as an artificial anus, the device including an absorbent flexible plug for insertion into the lumen of the passage, and an abutment portion in the form of a flexible adhesive sheet permanently or temporarily attached to the plug so as to hold the plug in position when also attached to the skin surrounding the opening, by connecting means which embrace the distal end of the plug. The plug is to be held so that it will neither move so far into the lumen of the opening that it may not be easily removed, nor will it come completely out of the opening, thereby failing to occlude it. The plug is preferably disposable and most suitably provided in the form of a tampon.

BRIEF DESCRIPTION OF THE DRAWINGS

In the accompanying drawings:

FIG. 1 is a cross-sectional side elevation of a device of the invention having an abutment in the form of a ferrule with a closure plug in place; and FIG. 2 is a side elevational view, partially in cross section, of a ferrule for a replaceable closure plug in accordance with the invention and a cooperating closure plug for the ferrule.

DETAILED DESCRIPTION

According to a particular aspect of the present invention we provide an abutment, for an external opening in an internal passage of a living body, comprising a flexible adhesive sheet adapted to retain an absorbent flexible closure plug replaceably within the lumen of the passage by means embracing the distal end of the plug whereby the plug may be replaced without detaching the abutment from the opening. In general the plug is fitted in the passage by insertion through an opening in the adhesive sheet corresponding to the opening in the body.

The means embracing the distal end of the plug may take any suitable form. For example the plug may be equipped with bayonet means, or simply a transverse pin, to cooperate for locking with slots in a ring on the abutment. The plug may alternatively be constructed, e.g. by means of a cap or ring, to make a press fit, or a snap fit, in a ring on the abutment. The embracing means may surround the distal end of the plug completely or only partly, e.g. by two or more separate resilient ring segments acting as a clamp. Locking devices such as those employing crossed elliptical members may also be utilised. A suitably capped plug which penetrates the abutment may be held in place by a simple adhesive strip over the outside of the abutment.

The adhesive sheet will normally be supplied with a releasable facing layer to protect the adhesive before use in the manner usual for adhesive dressings.

It is known to provide a device, covering an artificial anus, with a permeable section incorporating a filter made of, for example, charcoal, to allow the passage of flatus whilst reducing or eliminating the characteristic odour. Such a device may be incorporated in the present invention.

The preferred closure plug is approximately cylindrical in shape, being from 30 to 200 mm long, preferably 70–100 mm long and from 10 to 75 mm in diameter, preferably 20–35 mm in diameter. Artificial and other openings such as ani vary greatly in size and although the plug should be large enough to be firmly held in place, it should not be so large as to enlarge or permanently deform the opening. The plug may be constructed from a wide variety of materials, which should be flexible, absorbent, non-irritating and permeable to air. For example, foam plastics or rubber, wads or rolls of paper, conventional textile or nonwoven fabrics, may be used, or fibrous material such as cotton wool, wool, wood pulp, or rayon stable fibre, though if a fibrous material is used, it should be covered to prevent loss of fibre into the lumen of the intestine. Any of the nonfibrous materials mentioned above, or a perforated condom would form a suitable covering.

The abutment portion is constructed from flexible adhesive material. Many such materials, with either textile, nonwoven fabric, or plastics backings supporting a pressure-sensitive adhesive are known in the art as conventional surgical adhesive dressing. Since in this application, the adhesive material will be in constant contact with the skin and frequently removed and replaced, the adhesive material should be one which has minimal irritant effect on the skin. The abutment portion should be of sufficient size to adhere firmly to the skin, in order to hold the plug securely. The exact size and shape is not important, an adhesive area of 50–100 cm$^2$ being likely.

The closure plug may be attached to the abutment portion by a variety of means. Such means are illustrated in the accompanying drawings. In FIG. 1, the closure plug 10 is attached to the abutment portion 11 by a plastics ferrule 12 being held in place by the teeth 13 disposed from the inner wall of hollow cylindrical section 14. Flange 15 which is disposed about the distal end of said section 14 provides means for adhesively attaching to abutment portion 11 at the adhesive surface 16 thereof. Such a form may easily be fabricated in thermoplastic materials by vacuum thermoforming or any other of the techniques known in the art, and has the additional advantages of first, being attached to the adhesive abutment portion over a greater area than the above-mentioned devices, second, proving a protective nonadhesive shield over the suture line between abdominal and intestinal walls (an area particularly sensitive to the irritant effects of adhesives or exudate from the stoma) and third, a flatus filter 17 as described above may be conveniently located in the base.

In a further embodiment of the invention, note is taken that the frequent removal and replacement of an adhesive material from and to the area surrounding the stoma can cause severe irritation and discomfort of the skin. In order to reduce this effect, FIG. 2 illustrates a device of the above type in which the adhesive abutment portion and a ferrule similar to that shown in FIG. 1 are intended to remain in place for an extended period, such as two days, or perhaps a week, and the closure plug, which may be removed more frequently and replaced, is held temporarily and securely by mechanical means such as a bayonet type lock as is used in domestic electric light bulbs. Here a collar 18, preferably of plastic, surrounds and grips the distal end of the closure plug. Two or more lateral projections 19 engage corresponding L-shaped grooves 20 on the inner surface of the ferrule, providing a push-and-twist locking device. The unnumbered components of the device of FIG. 2 correspond to those identified by numbers in FIG. 1.

Components of the device of the present invention may advantageously carry or be coated with a hydrocolloidal gel such as is described in our British Pat. No. 13451/76, having beneficial water absorbency, antibacterial and lubricious properties.

What is claimed is:

1. An accessory for providing closure for a body orifice which comprises an absorbent flexible closure plug including a distal and a proximal end, said proximal end being capable of being introduced into said body orifice, and an abutment portion suitable for laying on the outside of the body, said abutment portion including attachment means capable of holding the distal end of said plug to said abutment portion so as to restrict said plug from being introduced too far into said orifice while insuring the occlusion thereof, said attachment means comprising means embracing said distal end of said plug, said abutment portion comprising a flexible adhesive sheet.

2. The accessory of claim 1 wherein said plug is a tampon.

3. The accessory of claim 1 wherein said plug is cylindrical in shape, being from 30 to 200 mm long and 10 to 75 mm in diameter.

4. The accessory of claim 1 wherein said abutment portion comprises a flexible adhesive material such as a pressure sensitive adhesive supported by a textile, nonwoven fabric or plastic backing.

5. The accessory of claim 4 wherein the adhesive area of said abutment portion is from 50 to 100 cm$^2$.

6. The accessory of claim 1 wherein said attachment means include a plastic ferrule, said ferrule including a (1) hollow cylindrical section and having a distal and proximate end, (2) a flange axially disposed about said distal end of said section, and (3) a plurality of L shaped grooves extending from said distal end of said section, said ferrule being adhesively secured to said abutment portion by said flange.

7. An accessory for providing closure for a body orifice which comprises an absorbent flexible closure plug including a distal and a proximal end, said proximal end being capable of being introduced into said body orifice, and an abutment portion suitable for laying on the outside of the body, said abutment portion including attachment means capable of holding the distal end of said plug to said abutment portion so as to restrict said plug from being introduced too far into said orifice while insuring the occulsion thereof, said abutment portion comprising a flexible adhesive sheet, said attachment means including a plastic ferrule, said ferrule including a (1) hollow cylindrical section and having a distal and proximal end, (2) a flange axially disposed about said distal end of said section, and (3) a plurality of teeth disposed about the internal wall of said section at a point spaced from said distal end, said ferrule being adhesively secured to said abutment portion by said flange.

8. The accessory of claim 7 wherein the adhesive area of said abutment portion is from 50 to 100 cm$^2$.

9. The accessory of claim 7 wherein said plug is a tampon.

10. The accessory of claim 7 wherein said plug is cylindrical in shape, being from 30 to 200 mm long and 10 to 75 mm in diameter.

* * * * *